(12) United States Patent
Kantrowitz et al.

(10) Patent No.: US 10,791,984 B2
(45) Date of Patent: Oct. 6, 2020

(54) ACTIVE HERMETICITY MONITORING

(71) Applicant: VIADERM, LLC, Ann Arbor, MI (US)

(72) Inventors: Allen B. Kantrowitz, Ann Arbor, MI (US); Chris Mortis, Ann Arbor, MI (US); Bradley Poff, Ann Arbor, MI (US)

(73) Assignee: Viaderm, LLC., Ann Arbor, MI (US)

( * ) Notice: Subject to any disclaimer, the term of this patent is extended or adjusted under 35 U.S.C. 154(b) by 290 days.

(21) Appl. No.: 15/125,273

(22) PCT Filed: Mar. 12, 2015

(86) PCT No.: PCT/US2015/020262
§ 371 (c)(1),
(2) Date: Sep. 12, 2016

(87) PCT Pub. No.: WO2015/138783
PCT Pub. Date: Sep. 17, 2015

(65) Prior Publication Data
US 2017/0172488 A1    Jun. 22, 2017

Related U.S. Application Data

(60) Provisional application No. 61/952,120, filed on Mar. 12, 2014.

(51) Int. Cl.
*A61B 5/00* (2006.01)
*A61B 5/053* (2006.01)
(Continued)

(52) U.S. Cl.
CPC ............ *A61B 5/445* (2013.01); *A61B 5/0004* (2013.01); *A61B 5/0531* (2013.01);
(Continued)

(58) Field of Classification Search
CPC ..... A61B 5/445; A61B 5/0004; A61B 5/0531; A61B 5/145; A61B 5/441; A61B 5/447; A61M 39/0247; A61M 2039/0267
(Continued)

(56) References Cited

U.S. PATENT DOCUMENTS

| 5,028,906 A | 7/1991 | Moriya et al. |
| 7,704,225 B2 * | 4/2010 | Kantrowitz ............. A61F 2/022 604/174 |

(Continued)

OTHER PUBLICATIONS

S. Grimes, "Impedance measurement of individual skin surface electrodes", Medical and Biological Engineering and Computing, Nov. 1983, pp. 750-755, vol. 21, Department of Biomedical Engineering, Rikshospitalet, Oslo, Norway.
(Continued)

*Primary Examiner* — Pedro Philogene
(74) *Attorney, Agent, or Firm* — Avery N. Goldstein; Blue Filament Law PLLC

(57) ABSTRACT

A system for measuring and monitoring wound hermaticity of a patient is provided that includes one or more sensors for measuring parameters that correlate to a degree of wound hermaticity, where the one or more sensors are incorporated into the design of a percutaneous skin access device (PAD), a bone anchor, a wound dressing, or a bandage. The degree of wound hermaticity is related to impedance measurements performed on the patient's skin, via measurements of humidity in a vacuum line to the PAD or the bone anchor, or via measurements of local tissue oxygenation in the immediate vicinity of the PAD or the bone anchor interface with the patient's skin. The hermaticity measurement parameters are communicated by wired or wireless connection to a computing or a communication device for immediate or remote monitoring.

12 Claims, 4 Drawing Sheets

(51) Int. Cl.
  *A61B 5/145* (2006.01)
  *A61M 39/02* (2006.01)
(52) U.S. Cl.
  CPC ..... *A61B 5/14542* (2013.01); *A61M 39/0247* (2013.01); *A61B 5/053* (2013.01); *A61B 5/145* (2013.01); *A61B 5/441* (2013.01); *A61B 5/447* (2013.01); *A61M 2039/0267* (2013.01)
(58) Field of Classification Search
  USPC .......... 600/547, 350, 361, 380, 593; 604/43, 604/174, 175, 543
  See application file for complete search history.

(56) References Cited

U.S. PATENT DOCUMENTS

| | | | | |
|---|---|---|---|---|
| 2008/0001735 A1* | 1/2008 | Tran | ............... | G06F 19/3418 340/539.22 |
| 2008/0234599 A1* | 9/2008 | Chiao | ............... | A61B 5/0031 600/547 |
| 2010/0022990 A1* | 1/2010 | Karpowicz | ......... | A61M 1/0088 604/543 |
| 2011/0015591 A1* | 1/2011 | Hanson | ............... | A61B 5/0059 604/318 |
| 2012/0150149 A1* | 6/2012 | Kantrowitz | ............. | A61F 2/022 604/522 |

OTHER PUBLICATIONS

Henry C. Lukaski & Micheal Moore, "Bioelectrical impedance assessment of wound healing", Journal of Diabetes Science and Technology, Jan. 2012, pp. 209-212, vol. 6, issue 1, Diabetes Technology Society.

International Search Report dated Aug. 21, 2015 for International Application No. PCT/US2015/020262 filed Mar. 12, 2015.

* cited by examiner

ACTIVE HERMETICITY MONITORING

RELATED APPLICATIONS

This application claims priority benefit of U.S. Provisional Application Ser. No. 61/952,120 filed Mar. 12, 2014; the contents of which are hereby incorporated by reference.

FIELD OF THE INVENTION

The present invention in general relates to medical devices and systems and in particular to measurement of wound hermaticity that is correlated with establishment of intact biological barrier function of the stratum corneum layer of skin.

BACKGROUND OF THE INVENTION

A common problem associated with implantation of a percutaneous access device (PAD) is skin regeneration about the periphery of the device to form an immunoprotective seal against infection. New cell growth and maintenance is typically frustrated by the considerable mechanical forces exerted on the interfacial layer of cells. In order to facilitate skin regeneration about the exterior of a PAD, subject cells are often harvested and grown in culture onto PAD surfaces for several days prior to implantation in order to allow an interfacial cell layer to colonize PAD surfaces in advance of implantation. Unfortunately, cell culturing has met with limited acceptance owing to the need for a cell harvesting surgical procedure preceding the implantation procedure. Additionally, maintaining tissue culture integrity is also a complex and time-consuming task.

As an alternative to cell culturing on a percutaneous access device, vacuum assisted wound treatment about a percutaneous access device has been attempted. While DACRON® based random felt meshes have been used to promote cell regrowth in the vicinity of a wound, such felts have uncontrolled pore sizes that harbor bacterial growth pockets.

U.S. Pat. No. 7,704,225 to Kantrowitz solves many of these aforementioned problems by providing cell channeling contours, porous biodegradable polymers and the application of vacuum to promote cellular growth towards the surface the neck of a PAD. The facilitating of rapid cellular colonization of a PAD neck allows the subject to act as their own cell culture facility, and as such affords more rapid stabilization of the PAD, and lower incidence of separation and infection.

However, existing PAD designs lack the ability to monitor or measure the degree of wound hermaticity, and to correlate the establishment of an intact biological barrier function of the stratum corneum layer of skin surrounding a PAD. Therefore, there is a need for systems and methods that actively assess and monitor hermaticity in wound closure that are incorporated into the design of percutaneous skin access devices.

SUMMARY OF THE INVENTION

A system for measuring and monitoring wound hermaticity of a patient includes one or more sensors for measuring parameters that correlate to a degree of wound hermaticity, where the one or more sensors are incorporated into the design of a percutaneous skin access device (PAD), a bone anchor, a wound dressing, or a bandage. The degree of wound hermaticity is related to impedance measurements performed on the patient's skin, via measurements of humidity in a vacuum line to the PAD or the bone anchor, or via measurements of local tissue oxygenation in the immediate vicinity of the PAD or the bone anchor interface with the patient's skin. The hermaticity measurement parameters are communicated by wired or wireless connection to a computing or a communication device for immediate or remote monitoring.

A method for measuring and monitoring wound hermaticity of a patient is provided that includes placing one or more sensors for measuring parameters that correlate to a degree of wound hermaticity on the skin of a patient, where the one or more sensors are incorporated into the design of a percutaneous skin access device (PAD), a bone anchor, a wound dressing, or a bandage.

An oblique lip and groove percutaneous skin access device (PAD) is provided that includes a tube that inserts into and through a patient's epidermal layer, and a stabilizing entry cover that mates up with the tube with a lip that fits into a groove made in an inner wall at the top of the tube, where the lip and the groove are configured to facilitate a dressing removal with the stabilizing entry cover.

BRIEF DESCRIPTION OF THE DRAWINGS

The subject matter that is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

Figure 1:
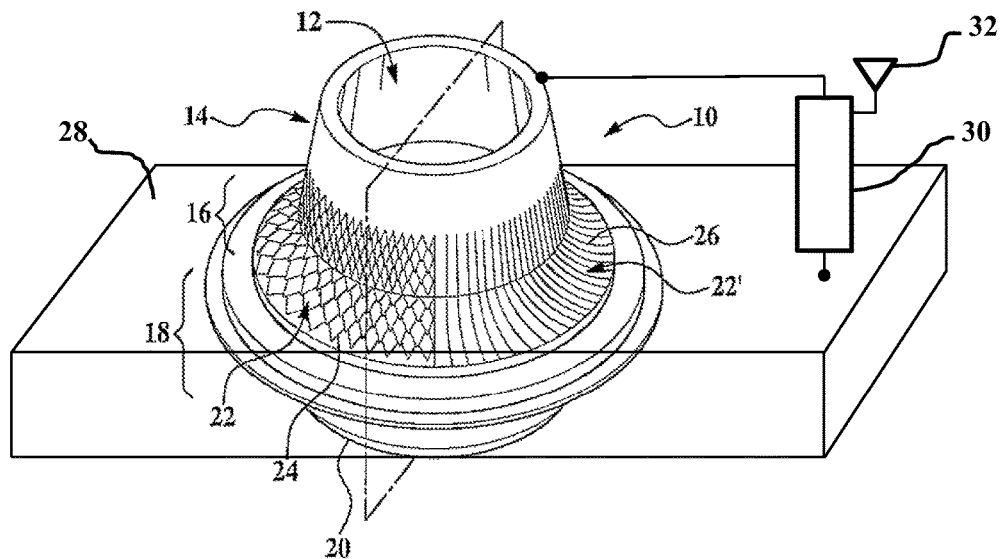
FIG. 1 is a composite perspective view depicting two exemplary cell growth channel pattern halves of an inventive percutaneous access device with hermaticity sensor embedded in the skin of a patient, where the cell growth channels are not depicted to scale for visual clarity according to embodiments of the invention.

The detailed description explains the preferred embodiments of the invention.

DESCRIPTION OF THE INVENTION

The present invention has utility as a system and method for measuring and monitoring wound hermaticity and correlating a hermaticity measurement with the establishment of intact biological barrier function of the stratum corneum layer of skin. Embodiments of the method and system for actively assessing hermaticity in wound closure are incorporated into the design of percutaneous skin access devices (PAD), bone anchors, or a wound dressing or bandage alone without at PAD. In a specific embodiment, the hermaticity of the skin wound in the vicinity of the skin-PAD interface is measured as a function of the fluid exudate or transudate egressing from the skin wound in the vicinity of the skin-PAD interface.

In certain embodiments of the present invention, the degree of hermaticity is related to impedance measurements performed on the skin of a patient. In a specific embodiment, an active impedance measurement may be performed as described in "Impedance measurements of individual surface electrodes" (Medical and Biological Engineering and Computing, November 1983, S. Grimnes) with two electrodes around the collar of a PAD, and/or the active impedance measurements incorporated into the PAD device. Impedance measurement of resistance (R), reactance (Xc), and phase angle (PA) have been shown to be effective in monitoring wound healing closure and infection as disclosed in "Bioelectrical Impedance Assessment of Wound Healing" (Journal of Diabetes Science and Tecchnology, January 2012, Lukaski et al.). As a wound heals resistance (R), reactance (Xc), and phase angle (PA) values increase, and if the wound is infected the values drop. Additional electrode patterns are possible which could further enhance the usefulness of the information.

In certain embodiments of the present invention, an assessment of hermaticity may be determined with measurements of humidity in the vacuum line to a PAD. The humidity readings may be taken with impedance humidity sensors. In still other embodiments, local tissue oxygenation in the immediate vicinity of the PAD or other measurements may be used to determine wound healing.

The hermaticity measurement parameters are readily communicated by wired or wireless connection to a computing or communication device for immediate or remote monitoring. Known and future wireless standards and protocols such as, but not limited to, Bluetooth, Zigbee, WiFi, and others may be used to transmit hermaticity measurements. Remote monitoring may be facilitated via an Internet or cellular network enabled device in communication with the output of a hermaticity measurement device or sensor. The hermaticity measurement devices or sensors may require an external power source such as a battery, or may be passive elements such as radio frequency identification elements (RFID), which obviate the need for an electrical power source to be directly incorporated into the PAD. A passive RFID element retransmits a signal using the energy of an incoming interrogation signal, where in embodiments of the inventive hermaticity sensor the transmitted signal will vary in frequency or phase with the impedance or humidity measurement. In certain embodiments, battery power used to supply the vacuum source of the PAD may also be utilized to supply power to the one or more hermaticity sensors.

The hermaticity sensor measurement information is readily employed for local closed-loop control of the vacuum supply to the PAD, and to alert the patient with regards to progress or problems with the PAD-skin interface. Additionally, the hermaticity information may be transmitted wirelessly to medical personnel to allow for remote monitoring of the healing wound. For example, as impedance or humidity in a vacuum line stabilizes, medical personnel may be notified that the wound has healed. Alternatively, if the impedance or humidity deviated from expected values, medical personnel could be notified that there may be an infection or a mechanical disruption to the wound; alarms could also be set to notify the patient. In an embodiment, the vacuum supplied to the PAD could automatically be increased or decreased based on the wound healing.

Referring now to the figures, FIG. 1 illustrates an inventive PAD 10 coupled to a hermaticity sensor 30. The stabilization of the PAD 10 within the skin to form a germ-free barrier requires subject cells to grow onto the neck surfaces 16 of the PAD 10 adjacent to the subject's epidermis 28. The portal 10 has an opening 12 defined by a sidewall 14, the exterior side of the wall 14 defining a neck region 16 adapted to promote growth of autologous fibroblast cells thereon. A suitable exterior side surface substrate for fibroblast growth is a nanotextured polycarbonate (LEXAN®). Beneath the neck region 16 lies an implanted region 18 terminating in an inward portal face 20, that is communicative with the opening 12 to form a passage through which fluids, electrical signals, gases or a combination thereof are communicated. The neck region 16 has a pattern of contoured autologous cell-conveying channels 22 or 22'. It is appreciated that the channels may take a variety of forms. In the figures, a linear channel 24 and a chrysanthemum-pattern channel 26 are depicted in composite halves as defined by the dashed plane. It is appreciated that an operative device typically would have a pattern 24 or 26 circumferentially decorating the device surface. Other channel patterns operative herein include any pattern that disfavors bacterial pocket formation. Optionally, a vacuum is drawn toward an upward region of the neck region 16 in order to actively draw blood plasma and fibroblasts contained therein along the channels 22 to further facilitate autologous cell growth on the neck region 16. Sensor 30 is operative to measure changes in impedance between the PAD 10 and the patient's skin 28 so as to determine hermaticity for the implanted PAD 10. Sensor 30 has wireless communication capabilities as represented by antenna 32 for transmitting sensor readings.

Figure 2:
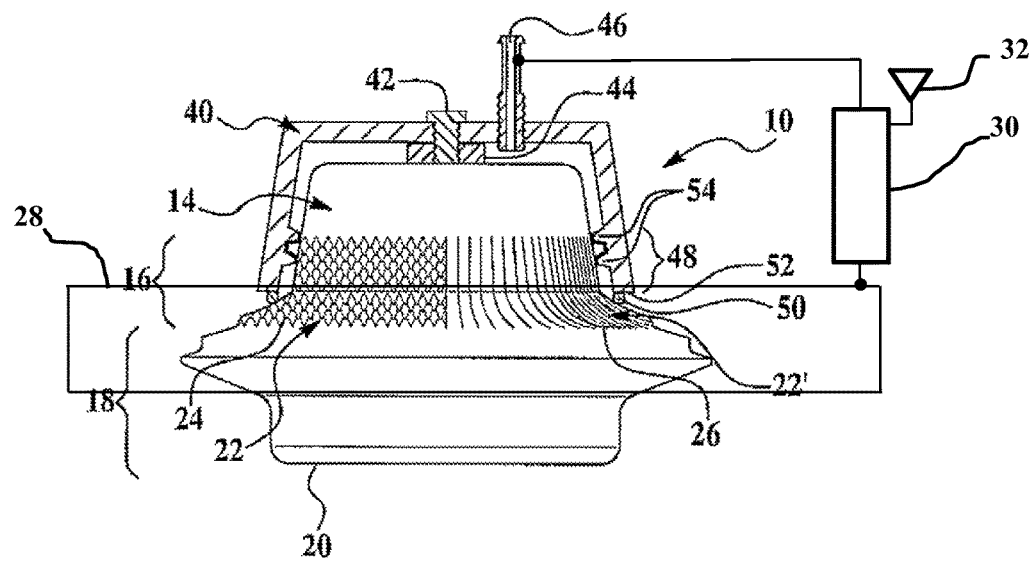
FIG. 2 is a plan view of the percutaneous access device depicted in FIG. 1 with a cross-sectional view along with a cross-sectional view of a vacuum manifold coupled thereto, and a sensor for detecting humidity levels in the vacuum line according to an embodiment of the invention.

Referring now to FIG. 2, a vacuum manifold 40 is secured to an inventive portal 10 by way of a fastener 42. The fastener 42 extends into a temporary seating pin (not shown) to fit within the opening 12. A spacer 44 assures a uniform gap between the manifold 40 and the neck region 16. An inlet 46 is provided for the coupling of the manifold 40 to a vacuum source. Manifold 40 has an extending lip 48 that terminates proximal to a surface of the neck portion 16 at at least one point amenable to form a seal 50 with the surrounding subject skin or a gel applied to the user skin. It is appreciated that a retaining groove 54 is defined on a lip surface in opposition to the portal neck portion 16, the retaining groove 54 amenable to seat a vacuum gasket between the manifold 40 and the neck portion 16. A gasket used herein is formed of conventional materials illustratively including neoprene. While the skin seal 50 is suitable to draw a vacuum around the periphery of the neck portion 16, cells that are drawn within the portal portion under vacuum tend to be drawn to a surface of the neck portion 16 as opposed to intercalating within a channel or a matrix coating. As such, it is appreciated that while drawing a vacuum at the interface between the neck portion 16 and lip terminus 52 is suitable to urge an initial population of cells into the channels 22, drawing of cells to the uppermost reaches of channels 22 preferably occurs by forming a vacuum seal between the manifold 40 and the neck portion 16 that includes only the uppermost terminus of the channels 22. It is appreciated that once cells begin to adhere to a surface defining a portion of a channel 22, abrasion and indeed contact with that surface is preferably avoided. It is further appreciated that a retaining groove 54 and the ensuing vacuum seal formed between the manifold 40 and the neck portion 16 is readily moved relative to the neck portion 16 by varying the thickness of the spacer 44. While the manifold 40 is beneficial in drawing serum and the fibroblasts contained therein through the channels 22 in the neck portion 16, it is also appreciated that independent of vacuum, the manifold 40 also serves to provide a mechanical guard to protect growing cells on the neck portion 16. To this end, it is appreciated that an inlet 46 can be connected to a gas supply such as air or oxygen to promote autologous cell growth and granulation about the neck portion 16; or liquid solutions fostering cell growth are also provided and illustratively include autologous plasma, fibroblast growth enhancing solutions, and antimicrobials. Sensor 30 can determine hermaticity with measurements of humidity in the vacuum line 46 to the PAD 10. Alternatively, the sensor may determine the hermaticity of the skin wound in the vicinity of the skin-PAD interface as measured as a function of the fluid exudate or transudate egressing from the skin wound in the vicinity of the skin-PAD interface.

Figure 3:
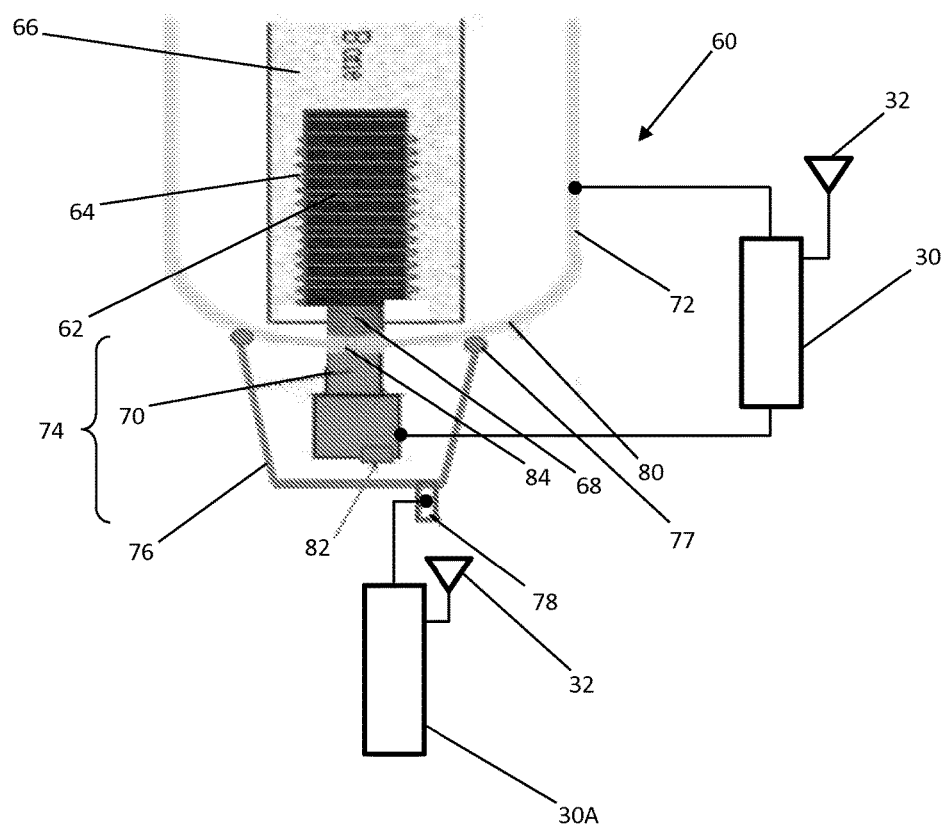
FIG. 3 illustrates a side sectional view of an embodiment of a bone anchor implanted in a bone with an attached abutment and negative pressure manifold applied and out-fitted with a hermaticity sensor for detecting resistance between the skin and a bone implant, and a sensor for detecting humidity in the vacuum line according to an embodiment of the invention.
Figure 4A:
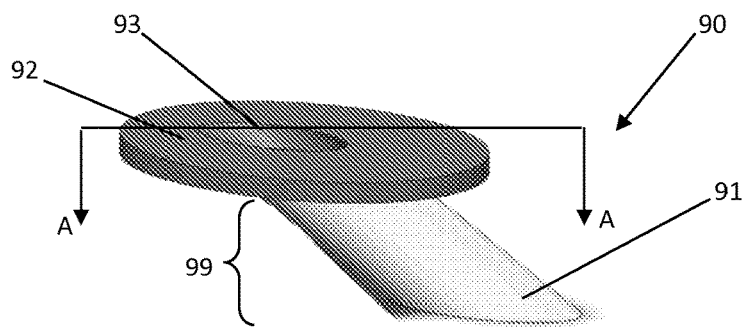
FIGS. 4A-4D are a series of views of an oblique lip and groove design for a percutaneous access device according to an embodiment of the invention.
Figure 4B:
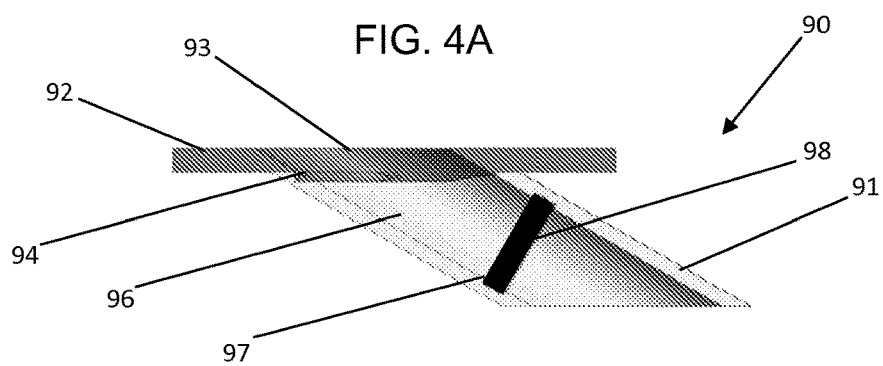
Figure 4C:
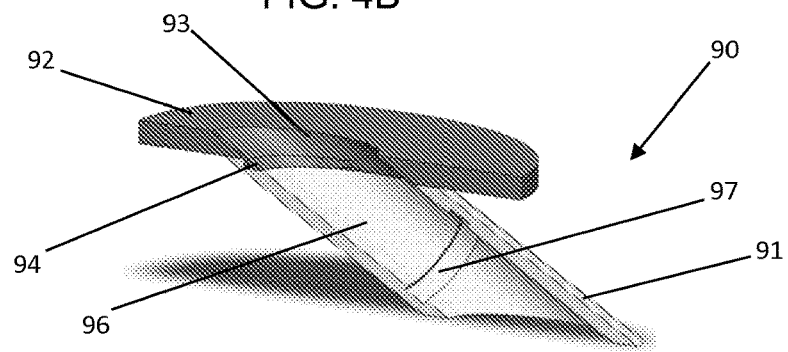
Figure 4D:
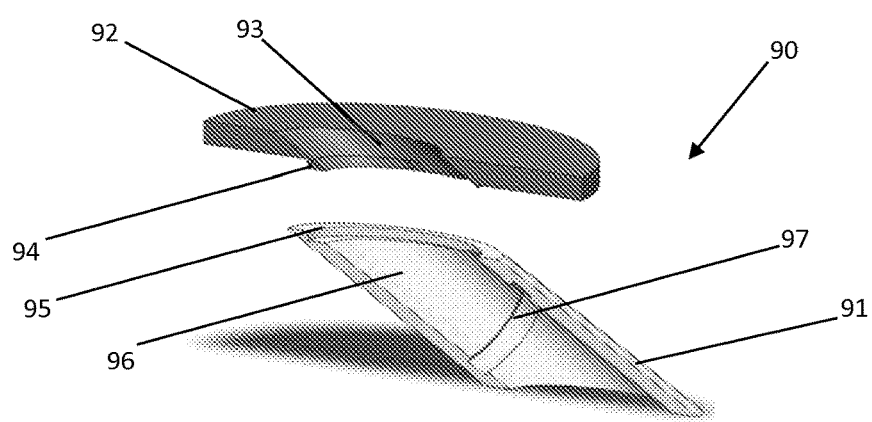

FIG. 3 illustrates an inventive bone anchor system 60 coupled to a sensor 30. The bone anchor system 60 includes the bone anchor 62 with a threaded screw portion 64 that engages and anchors into the bone 66 with a neck portion 68 extending out of the bone 66 and configured to mechanically engage an abutment 70 and biologically meld or engage with an epidermal or gum layer 72. The bone anchor system 60 also includes a negative pressure system 74 including a manifold 76 with an access point or inlet 78 that is fitted over the terminus or stump 80 of the wounded limb or region that encompasses the insertion point of the bone anchor 62. Manifold 76 may also be representative of a wearable dental appliance. Gasket 77 along the perimeter edge of the manifold 76 acts as a seal to the epidermal or gum layer 72. Access point 78 is configured to connect to a vacuum device for vacuum therapy in order to remove exudate and directly appose both soft and hard tissue to the bone anchor 62 and neck portion 68. Vacuum access 82 provides negative pressure access to microtexture/bone site interface of the neck portion 68, and is sealed following use. Tissue scaffold matrix 84 is a coating applied to the neck region 68 prior to implantation also that facilitates and promotes cell growth of autologous fibroblast cells thereon to make a seal with the epidermal or gum layer 72. A suitable exterior side surface substrate for fibroblast growth is a nanotextured polycarbonate (LEXAN®). Sensor 30 is operative to measure changes in impedance between the bone anchor 62 and the patient's epidermal or gum layer 72 so as to determine hermaticity for the implanted bone anchor 62. Sensor 30 has wireless communication capabilities as represented by antenna 32 for transmitting sensor readings. Sensor 30A may determine hermaticity with measurements of humidity in the vacuum line or access point 78 to the bone anchor system 60.

FIGS. 4A-4D are a series of views of an oblique lip and groove design for a percutaneous access device 90 according to an embodiment of the invention. The PAD 90 has a tube 91 that inserts into and through a patient's epidermal layer, and a stabilizing entry cover 92 that mates up with the tube 91 with a lip 94 that fits into a groove 95 made in the inner wall 96 at the top of the tube 91. The lip 94 and groove 95 is designed to facilitate dressing removal with stabilizing entry cover 92. The entry cover 92 is in the shape of a disk with an entry portal 93 that rest on the outer surface layer of a patient's epidermis and adds support and prevents movement of the tube 91 when devices are inserted into the PAD 90. The entry portal 93 is aligned with the tube 91. The tube 91 and entry portal 93 are shown as circular, however other shapes such as oval may also be used. The inner wall 96 has a retaining groove 97 for an o-ring or gasket 98 that seals against an inserted instrument when a vacuum is applied to the PAD 90. The o-ring or gasket 98 may be made of silicon. The exterior side of the wall defining a neck region 99 of the tube 91 is adapted to promote growth of autologous fibroblast cells thereon. A suitable exterior side surface substrate for fibroblast growth is a nanotextured polycarbonate (LEXAN®). In certain embodiments the surface of the tube 91 including the neck region 99 and/or the bottom portion of the stabilizing entry cover 92 are etched by a laser or by a chemical treatment to obtain a surface finish or roughness to promote cell growth attachment to the surface of the tube 91 and/or the stabilizing entry cover 92. In other embodiments the surface of the tube 91 and/or the bottom portion of the stabilizing entry cover 92 are embossed to obtain a surface finish or roughness to promote cell growth attachment to the surface of the tube 91 and/or the stabilizing entry cover 92.

In specific embodiments of the inventive PADs of FIGS. 1-4, an electrical stimulus or current may be applied across the wound area or at the PAD wound interface to stimulate and promote tissue repair. The electrical stimulus or current may be continuous direct current, an alternating current (AC), or pulsed at a defined frequency as a square wave or a ramped function.

Figure 5:
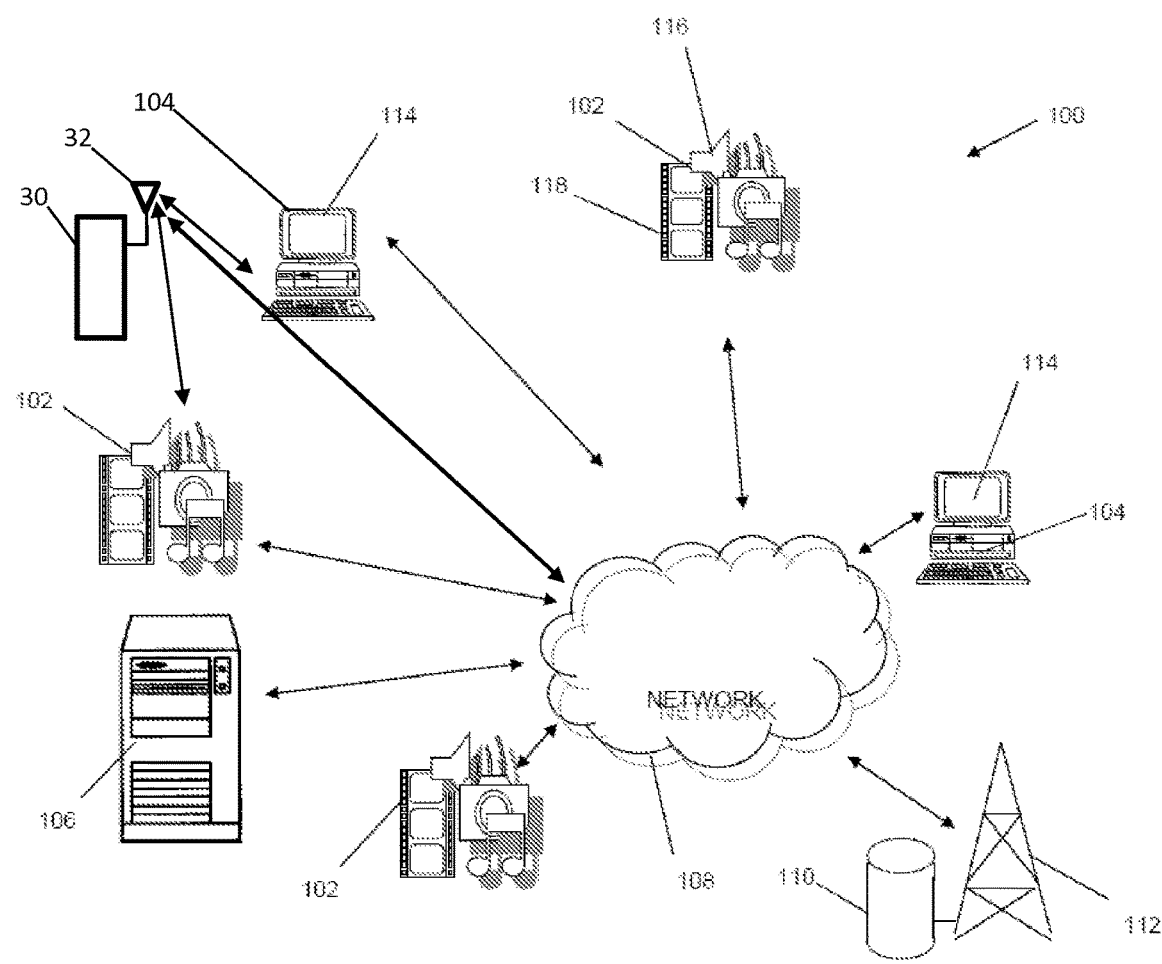
FIG. 5 is a schematic diagram illustrating an overall view of communication devices, computing devices, and mediums for implementing embodiments of the invention.

FIG. 5 is a schematic diagram illustrating an overall view of communication devices, computing devices, and mediums for implementing the hermaticity measuring and monitoring platform according to embodiments of the invention. The elements of the embodiments of FIGS. 1-4 are included in the networks and devices of FIG. 5.

The system 100 includes multimedia devices 102 and desktop computer devices 104 configured with display capabilities 114 and processors for executing instructions and commands. The multimedia devices 102 are optionally mobile communication and entertainment devices, such as cellular phones and mobile computing devices that in certain embodiments are wirelessly connected to a network 108. The multimedia devices 102 typically have video displays 118 and audio outputs 116. The multimedia devices 102 and desktop computer devices 104 are optionally configured with internal storage, software, and a graphical user interface (GUI) for carrying out elements of the hermaticity measuring and monitoring platform according to embodiments of the invention. The network 108 is optionally any type of known network including a fixed wire line network, cable and fiber optics, over the air broadcasts, satellite 120, local area network (LAN), wide area network (WAN), global network (e.g., Internet), intranet, etc. with data/Internet and remote storage capabilities as represented by server 106. Communication aspects of the network are represented by cellular base station 110 and antenna 112. In a preferred embodiment, the network 108 is a LAN and each remote device 102 and desktop device 104 executes a user interface application (e.g., Web browser) to contact the server system 106 through the network 108. Alternatively, the remote devices 102 and 104 may be implemented using a device programmed primarily for accessing network 108 such as a remote client. Hermaticity sensor 30 may communicate directly with remote devices 102 and 104 via near field communication standards such as Bluetooth or Zigbee, or alternatively via network 108.

The software for the platform, of certain inventive embodiments, is resident on multimedia devices 102, desktop or laptop computers 104, or stored within the server 106 or cellular base station 110 for download to an end user. Server 106 may implement a cloud-based service for implementing embodiments of the platform with a multi-tenant database for storage of separate client data.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A system for measuring and monitoring wound hermaticity of a patient comprising:
   an impedance sensor for measuring impedance in terms of resistance (R), reactance (Xc), and phase angle (PA) parameters that correlate to a degree of wound hermaticity;
   a vacuum source for drawing a vacuum on the wound around or under a percutaneous skin access device (PAD), a bone anchor, a wound dressing, or a bandage;
   wherein said impedance sensor is incorporated into the design of said percutaneous skin access device (PAD), said bone anchor, said wound dressing, or said bandage;
   wherein said degree of wound hermaticity is related to changes in impedance measurements between said PAD, said bone anchor, said wound dressing, or said bandage; and the patient's skin; and
   wherein said impedance sensor further comprises two electrodes a first electrode positioned on one of said PAD, said bone anchor, said wound dressing, or said bandage and a second electrode at the patient's skin.

2. The system of claim 1 wherein said hermaticity measurement parameters are communicated by wired or wireless connection to a computing or a communication device for immediate or remote monitoring.

3. The system of claim 2 wherein wireless connection is made via at least one of Bluetooth, Zigbee, or Wifi.

4. The system of claim 2 wherein said remote monitoring is via an Internet or cellular network enabled device in communication with said one or more sensors.

5. The system of claim 1 wherein said impedance sensor requires an external power source.

6. The system of claim 5 wherein said external power source is a battery used to supply a vacuum source to said PAD or said bone anchor.

7. The system of claim 1 wherein said impedance sensor has passive elements which do not require an external power source.

8. The system of claim 7 wherein said passive elements are radio frequency identification elements (RFID).

9. The system of claim 1 wherein said sensor parameters are employed for local closed-loop control of a vacuum supply to said PAD or said bone anchor.

10. A method for measuring and monitoring wound hermaticity of a patient comprising:
    placing a sensor for measuring impedance parameters that correlate to a degree of wound hermaticity on the skin of a patient;
    drawing a vacuum on the wound around or under a percutaneous skin access device (PAD), a bone anchor, a wound dressing, or a bandage using a vacuum source;
    wherein said impedance measurement sensor is incorporated into the design of said percutaneous skin access device (PAD), said bone anchor, said wound dressing, or said bandage;
    wherein said placing of said impedance measurement sensor further comprises positioning two electrodes a first electrode positioned on one of said PAD, said bone anchor, said wound dressing, or said bandage and a second electrode on the patient's skin; and
    wherein said degree of wound hermaticity is related to changes in impedance measurements between said PAD, said bone anchor, said wound dressing, or said bandage and the patient's skin, where as a wound heals resistance (R), reactance (Xc), and phase angle (PA) values increase, and if the wound is infected the values drop.

11. The method of claim 10 wherein said hermaticity measurement parameters are communicated by wired or wireless connection to a computing or a communication device for immediate or remote monitoring.

12. The method of claim 10 wherein said sensor parameters are employed for local closed-loop control of a vacuum supply to said PAD or said bone anchor.

* * * * *